(12) United States Patent
Villa

(10) Patent No.: US 11,051,601 B2
(45) Date of Patent: Jul. 6, 2021

(54) BEARD SHAPING DEVICE

(71) Applicant: Raul Francisco Villa, Natalia, TX (US)

(72) Inventor: Raul Francisco Villa, Natalia, TX (US)

(*) Notice: Subject to any disclaimer, the term of this patent is extended or adjusted under 35 U.S.C. 154(b) by 532 days.

(21) Appl. No.: 15/998,443

(22) Filed: Aug. 15, 2018

(65) Prior Publication Data
US 2019/0053599 A1 Feb. 21, 2019

Related U.S. Application Data

(60) Provisional application No. 62/545,585, filed on Aug. 15, 2017.

(51) Int. Cl.
A45D 27/42 (2006.01)
A45D 24/36 (2006.01)
A61K 8/02 (2006.01)
A61Q 9/02 (2006.01)

(52) U.S. Cl.
CPC .............. *A45D 27/42* (2013.01); *A45D 24/36* (2013.01); *A61K 8/0212* (2013.01); *A61Q 9/02* (2013.01)

(58) Field of Classification Search
CPC ........ A45D 27/24; A45D 24/36; A45D 44/12; A45D 40/30
USPC .................................................. 132/319, 214
See application file for complete search history.

(56) References Cited

U.S. PATENT DOCUMENTS

| 8,082,927 | B2 | 12/2011 | Bonge | |
| D768,332 | S | 10/2016 | Esnard | |
| 2004/0237988 | A1* | 12/2004 | Maynard | A45D 24/36 132/214 |
| 2006/0013844 | A1* | 1/2006 | Meriaux | A45D 40/30 424/402 |
| 2009/0183750 | A1* | 7/2009 | Platt-Gregory | A45D 40/30 132/216 |
| 2009/0223530 | A1* | 9/2009 | Chapman | A45D 27/42 132/200 |
| 2011/0067718 | A1* | 3/2011 | Lee | A45D 40/00 132/200 |
| 2012/0234341 | A1 | 9/2012 | Kingery | |
| 2014/0170193 | A1* | 6/2014 | Myhre | A61K 8/442 424/401 |
| 2015/0020658 | A1 | 1/2015 | Eljaouhari | |
| 2016/0015607 | A1* | 1/2016 | Stevens | A61K 8/0208 206/389 |
| 2016/0255938 | A1 | 9/2016 | Brunett | |

OTHER PUBLICATIONS

Hazel Chua, Travelon Toiletry Sheets: There's a Sheet for That, Jan. 28, 2012, http://technabob.com/blog/2012/01/28/travelon-toiletry-sheets/, pp. 1-3 (Year: 2012).*

* cited by examiner

*Primary Examiner* — Tatiana L Nobrega
(74) *Attorney, Agent, or Firm* — Kowert, Hood, Munyon, Rankin & Goetzel, P.C.; Gareth M. Sampson

(57) ABSTRACT

A device for guiding grooming of facial hair on a face and methods for using the device are disclosed. The device may include a strip of flexible material with an adhesive surface. The adhesive surface may temporarily attach the strip to a face having at least some facial hair. At least one edge of the strip may have a selected shape. The strip may be positioned on the face to cover a portion of the facial hair to be retained on the face while allowing an exposed portion of the facial hair to be removed by a shaving device. At least some part of the exposed portion of the facial hair lies along the edge of the strip with the selected shape.

16 Claims, 3 Drawing Sheets

BEARD SHAPING DEVICE

PRIORITY CLAIM

This patent claims priority to U.S. Provisional Patent Application No. 62/545,585 to Villa, entitled "BEARD SHAPING DEVICE", filed Aug. 15, 2017, which is incorporated by reference in its entirety as if fully set forth herein.

BACKGROUND OF THE INVENTION

1. Field of the Invention

Embodiments disclosed herein relate to a device for shaping hair. Certain embodiments disclosed herein relate to a device for shaping beards and/or facial hair on a human face.

2. Description of the Relevant Art

Facial hair (e.g., beards) often grows irregularly in shape and lines on a person's face can look awkward and/or misshapen due to the irregular hair growth. Shaping a beard on a person's face may be an irritating process and/or require professional care. There are limited options for people to shape their own beards. Currently available techniques and/or devices may be ineffective and/or leave the beard with irregular or asymmetrical line shapes. As such, currently available methods may be frustrating to use. Thus, there is a need for simpler and more easily used devices and methods for shaping beards (or other facial hair) on a human face.

SUMMARY OF EMBODIMENTS

In certain embodiments, a device for guiding grooming of facial hair on a human face includes a substrate or strip of flexible material with an adhesive surface. The adhesive surface may be configured to temporarily attach the strip/substrate to a human face having at least some facial hair. At least one edge of the strip/substrate may have a selected shape. While attached to the human face, the strip may be positioned on the human face to cover a portion of the facial hair that is to be retained on the human face while allowing an exposed portion of the facial hair to be removed by a shaving device. At least some part of the exposed portion of the facial hair lies along the edge of the strip having the selected shape.

In certain embodiments, a method for grooming shaped facial hair on a human face includes attaching a strip/substrate of flexible material to a human face having at least some facial hair. The strip/substrate may be attached to the human face using an adhesive surface on the strip/substrate. The strip/substrate may have at least one edge with a selected shape. At least some facial hair may be removed from a portion of the human face exposed beyond one or more edges of the strip/substrate. At least some of the facial hair removed may include facial hair that lies along the edge of the strip/substrate with the selected shape. The strip/substrate may be removed from the human face after removing facial hair from exposed portion of the human face.

BRIEF DESCRIPTION OF THE DRAWINGS

Features and advantages of the methods and apparatus described herein will be more fully appreciated by reference to the following detailed description of presently preferred but nonetheless illustrative embodiments when taken in conjunction with the accompanying drawings in which.

Figure 1:
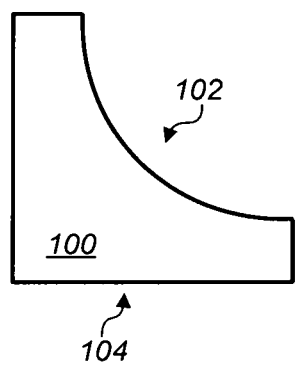
FIG. 1 depicts a representation of an embodiment of a facial hair shaping device.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form illustrated, but on the contrary, the intention is to cover all modifications, equivalents and alternatives falling within the spirit and scope of the present disclosure as defined by the appended claims. The headings used herein are for organizational purposes only and are not meant to be used to limit the scope of the description. As used throughout this application, the word "may" is used in a permissive sense (i.e., meaning having the potential to), rather than the mandatory sense (i.e., meaning must). Similarly, the words "include," "including," and "includes" mean including, but not limited to. Additionally, as used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The scope of the present disclosure includes any feature or combination of features disclosed herein (either explicitly or implicitly), or any generalization thereof, if it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

DETAILED DESCRIPTION OF EMBODIMENTS

The following examples are included to demonstrate preferred embodiments. It should be appreciated by those of skill in the art that the techniques disclosed in the examples which follow represent techniques discovered by the inventor to function well in the practice of the disclosed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosed embodiments.

This specification includes references to "one embodiment" or "an embodiment." The appearances of the phrases "in one embodiment" or "in an embodiment" do not necessarily refer to the same embodiment, although embodiments that include any combination of the features are generally contemplated, unless expressly disclaimed herein. Particular features, structures, or characteristics may be combined in any suitable manner consistent with this disclosure.

FIG. 1 depicts a representation of an embodiment of facial hair shaping device 100. Device 100 may be used to shape facial hair such as, but not limited to, beards, mustaches, sideburns, or other hair on a human face. Device 100 may be applied and/or attached to a human face (e.g., a user's face), as described herein, to allow the user (or another person) to shave or groom facial hair (e.g., a beard) on exposed parts of the user's face while facial hair covered by the device is inhibited or prevented from being shaved or groomed by the device. In certain embodiments, device 100 is used as a grooming substrate or strip to shape a beard (or other facial hair) on the user's face.

Figure 6:
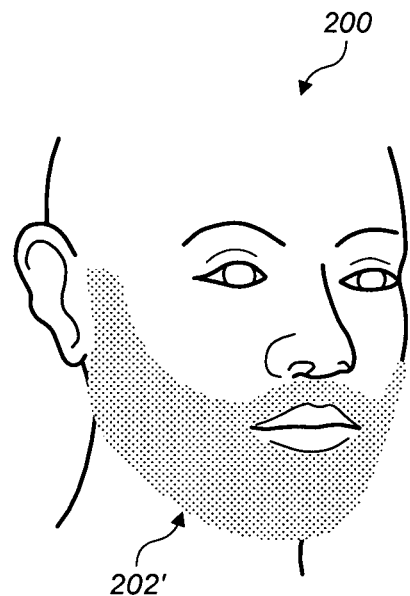
FIG. 6 depicts an embodiment of a human face with shaped facial hair after use of a curved edge of an embodiment of a facial hair shaping device described herein.
Figure 7:
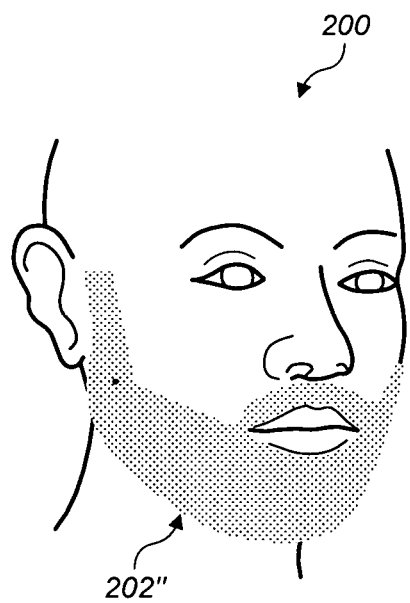
FIG. 7 depicts an embodiment of a human face with shaped facial hair after use of a straight edge of an embodiment of a facial hair shaping device described herein.

In certain embodiments, device 100 includes edges that are shaped to provide desired grooming lines for facial hair on the user's face. For example, in one embodiment, as shown in FIG. 1, device 100 includes curved edge 102 and straight edge 104. Curved edge 102 may be used to provide a curved grooming line to facial hair on the user's face (for example, as shown in the embodiment of FIG. 6). Straight edge 104 may be used to provide a straight grooming line to facial hair on the user's face (for example, as shown in the embodiment of FIG. 7). It is to be understood that while FIG. 1 depicts device 100 with curved edge 102 and straight edge 104, the shapes of the edges may be varied (e.g., varied based to provide a desired shape and/or a desired curve for the grooming line). For example, an edge may have an angled edge shape (e.g., two straight sections meeting at an angle), the edge may have a jagged edge shape, or the edge may have a wavy edge shape.

In some embodiments, multiple devices 100 with various shapes may be provided to and/or utilized by the user to allow the user to choose a selected shape for grooming when desired. For example, a kit may include a plurality of devices 100, with at least some of the devices having different shapes (e.g., edge shapes). In addition to the shapes of the edges, the design, size and/or overall shape of device 100 may also be varied as needed or desired.

Figure 2:
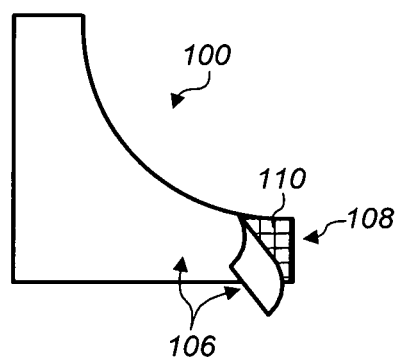
FIG. 2 depicts a representation of an embodiment of the facial hair shaping device with a layer being peeled off.
Figure 3:
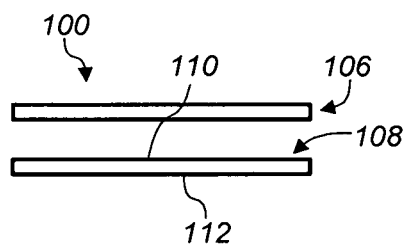
FIG. 3 depicts a side-view representation of a facial hair shaping device.
Figure 5:
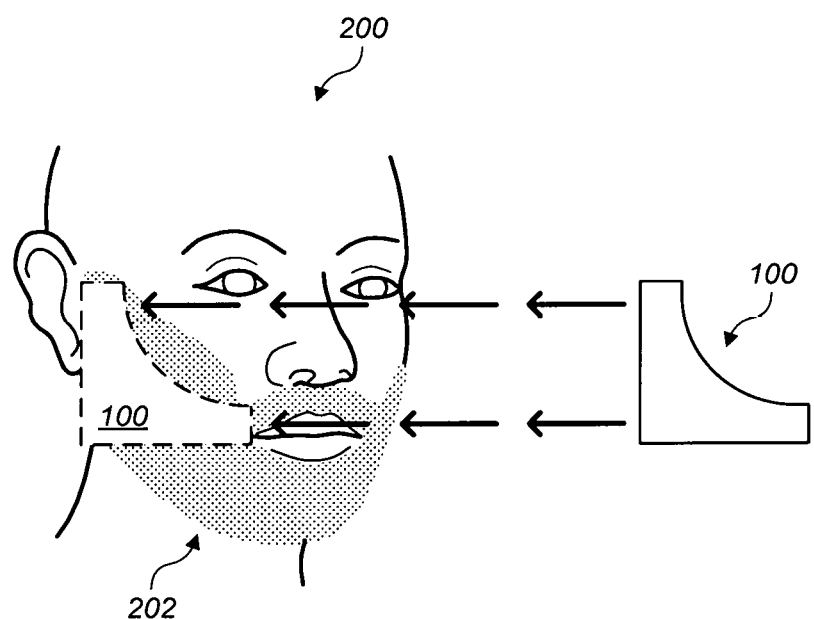
FIG. 5 depicts a representation of an embodiment of a facial hair shaping device applied to the human face of FIG. 4.

FIGS. 2 and 3 depict embodiments of device 100 showing the layers of the device. Device 100 may be, for example, a strip (or similar narrow band, ribbon, slab, or tape structure) having one or more layers of material. In some embodiments, the strip includes flexible material to allow the strip to contour to the user's face. In certain embodiments, device 100 includes protective layer 106 and adhesive layer 108. Protective layer 106 may protect adhesive surface 110 of adhesive layer 108 until device 100 is ready to be attached to (e.g., applied to) the user's face (e.g., the protective layer may protect the adhesive surface during handling and/or transport of device 100). Protective layer 106 may be removed to expose adhesive surface 110 (shown by the checkered pattern in FIG. 2). After exposure, adhesive surface 110 may be used to apply, couple, or attach device 100 to the user's face (as shown in the embodiment of FIG. 5). Thus, adhesive layer 108 may be the only layer of device 100 applied to the user's face as protective layer 106 is removed to expose adhesive surface 110.

Adhesive surface 110 may include adhesive materials for attaching (applying) device 100 to a user's face. In certain embodiments, adhesive surface 110 includes materials that attach to facial hair on the user's face. The user may press or apply pressure to device 100 to secure adhesive surface 110 to the user's face. The materials in adhesive surface 110 may, however, attach to the facial hair and be able to be gently removed from the user's face such that facial hair is not removed when device 100 is removed from the user's face. For example, adhesive surface 110 may include materials that gently adhere device 100 to both the user's face and facial hair on the user's face while allowing the device to be removed with a relatively light force. Allowing gentle removal of device 100 may also be a more pleasant experience for the user.

In certain embodiments, adhesive surface 110 covers substantially the entire surface (e.g., substantially the entire surface area) of the side of device 100 the adhesive surface is applied to (e.g., the adhesive surface covers all or almost all of the surface area on the side of the device). With adhesive surface 110 covering substantially the entire surface of the side of device 100, the device may be more securely attached to the user's face and facial hair to prevent slippage or movement during a shaving process. In such embodiments, the user may press or apply pressure over substantially the entire surface (e.g., all or almost all the surface) of device 100 to secure adhesive surface 110 to the user's face.

In some embodiments, adhesive surface 110 may be a surface that has adhesive properties activated by addition of another material to the adhesive surface. For example, adhesive surface 110 may be a surface with inactive adhesive properties where the adhesive properties of the surface are activated by the addition of another material such as an activation agent or activation fluid. In such embodiments, protective layer 106 may not be needed as adhesive surface 110 is not ready to be attached to the human face until the activation agent is provided to the adhesive surface (e.g., the adhesive surface will not accidentally attach to another surface until activated).

In some embodiments, a dye material is integrated in adhesive surface 110. The dye material may include, for example, hair and/or skin coloring material. In some embodiments, the dye material includes hair coloring material to change the color of the facial hair on the user's face (e.g., darken gray beard hair). In some embodiments, the dye material includes skin coloring material (or other dyes) that provide a fuller appearance to the facial hair remaining on the user's face after use of device 100.

In some embodiments, second surface 112 of adhesive layer 108 (shown in FIG. 3) includes one or more materials to aid in grooming of the facial hair on the user's face. For example, in some embodiments, second surface 112 includes a gel or other lubricant used for shaving facial hair. The gel may be, for example, a dry shaving gel that foams or otherwise lubricates when water is added. Providing a gel or other lubricant on second surface 112 may provide a more pleasant shaving experience for the user when using device 100.

Figure 4:
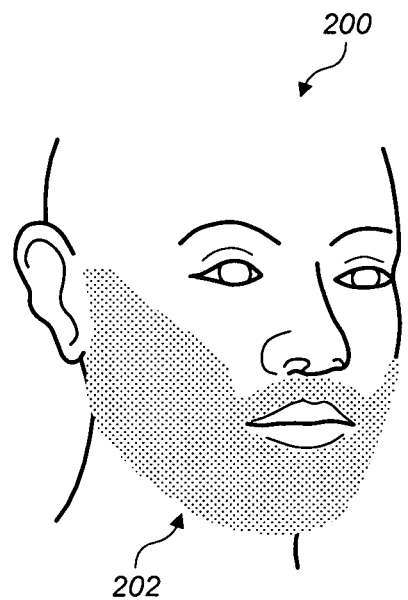
FIG. 4 depicts an embodiment of a human face with asymmetrical facial hair.

FIGS. 4, 5, 6, and 7 depict embodiments of the user's face 200 with facial hair 202 before, during, and after use of device 100. FIG. 4 depicts an embodiment of face 200 with asymmetrical facial hair 202. In certain embodiments, facial hair 202 is a beard on face 200 (e.g., an asymmetrical beard). In FIG. 5, device 100 is applied to face 200 over a portion of facial hair 202. Device 100 may be positioned by the user (or another person) such that the edges (e.g., curved edge 102 or straight edge 104) are positioned in desired locations on face 200. Device 100 may be placed over facial hair 202 such that the device covers portions of the facial hair that the user does not want to remove from face 200.

After device 100 is positioned and applied (e.g., attached) to face 200, the user (or another person) may remove exposed facial hair from the face. For example, the user may remove facial hair 202 that is exposed along and above curved edge 102. In some embodiments, the user uses a razor or other shaving device to remove exposed facial hair on face 200. In some embodiments, water is added to the dry lubricant to generate wet lubricant, which is spread onto one or more exposed portions and used during removal of facial hair from the human face.

After removing the exposed facial hair, device 100 may be removed from face 200, as shown in FIG. 6. Removing the exposed facial hair along and above curved edge 102 may provide shaped facial hair 202'. As shown in FIG. 6, facial hair 202' may have a neatly shaped curved edge after using device 100 (e.g., the user's face has a neatly shaped, symmetrical beard with a curved shape). FIG. 7 depicts an embodiment of user's face 200 after using a straight edge (e.g., straight edge 104) on device 100. As shown in FIG. 7, facial hair 202" may have a neatly shaped straight edge after using device 100 (e.g., the user's face has a neatly shaped, symmetrical beard with a straight line).

As described herein, device 100 provides a simple tool for providing shaped removal of facial hair from a user's face (e.g., a human face). Device 100 may be simple and inexpensive to allow a user to easily shape and/or groom the user's own face without the need for professional services (e.g., professional barbershop or salon services). Device 100 may have a variety of shapes and/or sizes to provide various different shapes or lines for grooming the user's face. Thus, a user may use one or more devices (such as device 100) to provide any desired shape and/or lines to the user's facial hair (e.g., the user's beard).

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

Further modifications and alternative embodiments of various aspects of the embodiments described in this disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as the presently preferred embodiments. Elements and materials may be substituted for those illustrated and described herein, parts and processes may be reversed, and certain features of the embodiments may be utilized independently, all as would be apparent to one skilled in the art after having the benefit of this description. Changes may be made in the elements described herein without departing from the spirit and scope of the following claims.

What is claimed is:

1. A shaving template for guiding grooming of facial hair on a human face, comprising:
    a substrate constructed of flexible material, the substrate having a first side with an adhesive surface configured to temporarily attach the substrate to a human face having at least some facial hair thereon, and a second side with a lubricating surface disposed opposite the adhesive surface, the lubricating surface comprises a dry shaving lubricant configured to lubricate the human face when water is added thereto;
    wherein the substrate defines an outer perimeter with at least one edge having a selected shape for guiding a user in shaving exposed facial hair adjacent the at least one edge;
    wherein, during use, the substrate is configured to be adhered via the adhesive surface to the human face to cover a portion of the facial hair which shall remain on the human face while leaving an exposed portion of the facial hair to be removed, and, water is added to the dry shaving lubricant to form a wet lubricant to be used in combination with a shaving device to remove at least some part of the exposed portion of the facial hair that lies along the at least one edge of the substrate.

2. The device of claim 1, wherein the selected shape of the at least one edge comprises a curved edge.

3. The device of claim 1, wherein the selected shape of the at least one edge comprises a straight edge.

4. The device of claim 1, wherein the at least one edge comprises at least one curved edge and at least one straight edge.

5. The device of claim 1, wherein the adhesive surface covers an entirety of the first side of the substrate.

6. The device of claim 1, further comprising a protective layer placed on the adhesive surface, wherein the protective layer is removed from the adhesive surface before attaching the strip to the human face.

7. The device of claim 1, further comprising a dye material integrated on the adhesive surface.

8. The device of claim 1, wherein the adhesive surface comprises an inactive adhesive surface until an activation agent is provided to the adhesive surface.

9. A method for grooming shaped facial haft on a human face, comprising:
    providing a substrate constructed of flexible material, the substrate having a first side with an adhesive surface and a second side with a lubricating surface disposed opposite the adhesive surface, the lubricating surface comprising a dry shaving lubricant, wherein the substrate defines an outer perimeter with at least one edge having a selected shape;
    attaching the substrate over a portion of the human face having facial hair thereon, wherein the substrate is attached to the human face via the adhesive surface;
    adding water to the dry shaving lubricant on the lubricating surface to generate a wet lubricant and spreading the wet lubricant to one or more exposed portions of the human face having facial hair to be removed;

removing at least some facial hair from the one or more exposed portions of the human face which includes facial hair that lies along the at least one edge with having, the selected shape; and removing the strip from the human face after removing the at least some facial hair from the one or more exposed portions of the human face.

10. The method of claim 9, wherein the removing the at least some facial hair from the one or more exposed portions of the human face comprises using a shaving device to remove the at least some facial hair.

11. The method of claim 9, wherein the selected shape of the at least one edge comprises a curved edge.

12. The method of claim 9, wherein the selected shape of the at least one edge comprises a straight edge.

13. The method of claim 9, wherein the at least one edge comprises at least one curved edge and at least one straight edge.

14. The method of claim 9, wherein little to no facial hair is removed from the human face by the substrate when the substrate is removed from the human face.

15. The method of claim 9, wherein the substrate comprises a protective layer placed on the adhesive surface, the method further comprising removing the protective layer from the adhesive surface before attaching the substrate to the human face.

16. The method of claim 9, wherein the adhesive surface covers an entirety of the first side of the substrate.

* * * * *

UNITED STATES PATENT AND TRADEMARK OFFICE
CERTIFICATE OF CORRECTION

PATENT NO. : 11,051,601 B2
APPLICATION NO. : 15/998443
DATED : July 6, 2021
INVENTOR(S) : Raul Francisco Villa It is certified that error appears in the above-identified patent and that said Letters Patent is hereby corrected as shown below:

In the Claims

Claim 9, Column 6, Line 54, after the word facial, please delete "haft" and add --hair--.

Claim 9, Column 7, Line 5, after the word facial, please delete "haft" and add --hair--.

Claim 10, Column 7, Line 11, after the word facial, please delete "haft" and add --hair--.

Signed and Sealed this
Thirty-first Day of August, 2021

Drew Hirshfeld
*Performing the Functions and Duties of the
Under Secretary of Commerce for Intellectual Property and
Director of the United States Patent and Trademark Office*